United States Patent [19]

Sasaki et al.

[11] Patent Number: 6,136,998
[45] Date of Patent: *Oct. 24, 2000

[54] RETENTION OF ACTIVITY OF MOLYBDENUM-CONTAINING METALLIC OXIDE CATALYST

[75] Inventors: Yutaka Sasaki; Kunio Mori; Yoshimi Nakamura; Kazuo Morishita; Ken Ohyachi, all of Yokohama, Japan

[73] Assignee: Mitsubishi Rayon Co., Ltd., Tokyo-To, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/948,296

[22] Filed: Oct. 10, 1997

[30] Foreign Application Priority Data

Oct. 15, 1996 [JP] Japan .................................. 8-291234

[51] Int. Cl.⁷ .................................................. C07C 255/00
[52] U.S. Cl. .................... 558/322; 558/323; 558/324; 502/302; 502/304; 502/305
[58] Field of Search ..................... 502/302, 304, 502/305, 306, 308, 310, 311, 317, 318, 319, 320, 321, 322, 323; 558/322, 323, 324

[56] References Cited

U.S. PATENT DOCUMENTS

| | | | |
|---|---|---|---|
| 4,278,614 | 7/1981 | Umemura et al. | 260/465.3 |
| 4,409,122 | 10/1983 | Kleuskens et al. | 502/20 |
| 4,456,563 | 6/1984 | Katsumata et al. | 260/465.8 R |
| 4,618,593 | 10/1986 | Sasaki et al. | 502/20 |
| 4,873,217 | 10/1989 | Kawajiri et al. | 502/311 |
| 5,212,137 | 5/1993 | Suresh et al. | 502/212 |
| 5,276,178 | 1/1994 | Onodera et al. | 562/537 |
| 5,422,328 | 6/1995 | Ushikubo et al. | 502/312 |
| 5,470,815 | 11/1995 | Kim et al. | 502/311 |

FOREIGN PATENT DOCUMENTS

| | | |
|---|---|---|
| 2279465 | 2/1976 | France . |
| 1286083 | 8/1972 | United Kingdom . |

OTHER PUBLICATIONS

Patent Abstracts of Japan, vol. 016, No. 544 (C–1004), Nov. 13, 1992, & JP 04 208239 A (Mitsubishi Rayon Co Ltd), Jul. 29, 1992.

Patent Abstracts of Japan, vol. 003, No. 083 (C–052), Jul. 18, 1979 & JP 54 061111 A (Ube Ind Ltd), May 17, 1979.

Primary Examiner—Joseph K. McKane
Assistant Examiner—Joseph Murray
Attorney, Agent, or Firm—Wenderoth, Lind & Ponack, L.L.P.

[57] ABSTRACT

In the gas phase oxidation of an organic compound, using a metallic oxide fluidized-bed catalyst that contains molybdenum in an amount of 10% by weight or more, bismuth, and at least an element selected from the group consisting of iron and cerium, when tellurium is incorporated into this catalyst in such an amount that the atomic ratio of the tellurium to the molybdenum is (0.05–1.5):10, the catalytic activity can be retained for a prolonged period of time, and, at the same time, the loss of molybdenum and tellurium can be prevented during the oxidation reaction.

3 Claims, No Drawings

RETENTION OF ACTIVITY OF MOLYBDENUM-CONTAINING METALLIC OXIDE CATALYST

BACKGROUND OF THE INVENTION

1. Field of the Invention

The present invention relates to a method for retaining the activity of molybdenum-containing metallic oxide catalysts which are used, for example, for the oxidation (including ammoxidation and oxidative dehydrogenation) of organic compounds that is conducted by means of gas phase fluidized-bed reaction at high temperatures.

2. Related Art

It has been known that molybdenum-containing metallic oxide catalysts are useful for the oxidation (including ammoxidation and oxidative dehydrogenation) of organic compounds. These catalysts are used, for instance, for producing acrolein or acrylic acid by means of the oxidation of propylene; for producing acrylonitrile by means of the ammoxidation of propylene; for producing methacrolein or methacrylic acid by means of the oxidation of isobutene or tert-butanol; for producing methacrylonitrile by means of the ammoxidation of isobutene or tert-butanol; for producing acrylonitrile by means of the ammoxidation of propane; for producing methacrylonitrile by means of the ammoxidation of isobutane; for producing formaldehyde by means of the oxidation of methanol, methylal or the like; for producing hydrogen cyanide by means of the ammoxidation of methanol; and for producing butadiene or the like by means of the oxidative dehydrogenation of n-butene. In addition, the catalysts are also used for the oxidation or ammoxidation of alkyl aromatic hydrocarbons or alkyl heteroaromatic compounds.

As the molybdenum-containing metallic oxide catalysts for use in the above-described reactions, there can be mentioned those which are described in Japanese Patent Publication No. 3563/1961 (U.S. Pat. No. 2,941,007), Japanese Patent Publication No. 27490/1972 (U.S. Pat. No. 3,959,384), Japanese Patent Publication No. 5870/1971 (U.S. Pat. No. 2,904,580), Japanese Patent Publication No. 33888/1976 (U.S. Pat. No. 4,503,001), Japanese Patent Laid-Open Publication No. 47319/1974 (U.S. Pat. No. 3,898,267), Japanese Patent Laid-Open Publication No. 16887/1973 (U.S. Pat. No. 4,036,870), Japanese Patent Laid-Open Publication No. 257/1990 (U.S. Pat. No. 5,049, 692), Japanese Patent Publication No. 35400/1976 (U.S. Pat. No. 3,911,089), Japanese Patent Publication No. 39005/1977 (U.S. Pat. No. 3,801,670), Japanese Patent Publication No. 44249/1985, Japanese Patent Laid-Open Publication No. 223812/1995, Japanese Patent Publication No. 14659/1981 (U.S. Pat. No. 3,803,204), Japanese Patent Laid-Open Publication No. 111565/1977 (U.S. Pat. No. 4,055,511), and the like. Catalysts containing both molybdenum and tellurium have also been proposed, and are described in Japanese Patent Publication No. 41583/1987 (U.S. Pat. No. 4,446, 328), Japanese Patent Publication No. 41584/1987 (U.S. Pat. No. 4,446,328), Japanese Patent Publication No. 41585/1987 (U.S. Pat. No. 4,446,328), Japanese Patent Laid-Open Publication No. 70922/1974 (GB Patent No. 1,415,766), Japanese Patent Laid-Open Publication No. 38330/1980 (U.S. Pat. No. 4,278,614), Japanese Patent Publication No. 38424/1983 (U.S. Pat. No. 3,969,390), Japanese Patent Publication No. 38425/1983 (U.S. Pat. No. 3,928,409), Japanese Patent Laid-Open Publication No. 114560/1982, Japanese Patent Laid-Open Publication No. 130549/1982 (GB Patent No. 2,090,156), Japanese Patent Laid-Open Publication No. 228950/1989, Japanese Patent Laid-Open Publication No. 118051/1992 (U.S. Pat. No. 5,132,269), Japanese Patent Publication No. 16971/1980, and the like.

Although these molybdenum-containing metallic oxide catalysts have excellent properties, it is known that the molybdenum component is lost from many of the catalysts especially when the reaction temperature is high, thereby causing various troubles such as deterioration in the properties of the catalysts, and the deposition of molybdenum on the inside of the reaction system (J. Bulten, J. Catal., 10, 188–199 (1968); G. P. Wing, L. B. Sis, J. S. Wheeler, J. Catal., 38, 196–205 (1975); I. Nicolau, A. Aguilo, P. B. DeGroot, 4th Inter. Conf. Chem., Uses of Molybdenum, 1982, 234–240; etc.).

Molybdenum component is considered to be lost in the following way: molybdenum trioxide in the catalyst reacts with water in the reaction gas to yield volatile $MoO_2(OH)_2$, and thus is lost from the catalyst.

To solve this problem, studies were made with the aim of decreasing the amount of free molybdenum trioxide by modifying the composition of the catalyst, thereby converting the free molybdenum trioxide into molybdates. However, this is not necessarily satisfactory because it is difficult to make the results of reaction and the life or properties of the catalyst compatible with each other.

Further, studies were also made to lower the reaction temperature. Regarding fixed-bed reaction, those catalysts which are active even at low temperatures were searched, and prevention of the occurrence of hot spots was also tried. The problem was thus solved to some extent in the oxidation of olefins. However, in those reactions which are carried out at higher temperatures, for example, in ammoxidation reaction of an olefin, the problem of the loss of molybdenum component tends to become an issue more often.

The loss of molybdenum component is thus considered to be unavoidable to some extent, so that a method is usually adopted such that the activity of a molybdenum-containing catalyst is retained by replenishing the molybdenum component during reaction. When the reaction is fixed-bed reaction, there have been used, as the method of this type, those methods which are described in Japanese Patent Publication No. 1848/1966, British Patent Publication No. 814,075, Japanese Patent Laid-Open Publications No. 193136/1984 and No. 10799/1995 (U.S. Pat. No. 5,602, 280), etc.; and when fluidized-bed reaction, those methods which are described in Japanese Patent Publication No. 57422/1983, German Patent Publication No. 3,311,521, Japanese Patent Laid-Open Publication No. 301051/1993, etc. All of these methods are such that molybdenum oxide or a molybdenum compound, or molybdenum oxide or a molybdenum compound supported on an inert carrier, or a molybdenum-component-enriched catalyst is added to the reaction system in order to make up the molybdenum component which has been depleted from the catalyst used. Although the catalytic activity can be retained to some extent by these methods, they are troublesome because it is necessary to continuously and repeatedly replenish molybdenum component in a short period of time. In addition, it is difficult, especially in the case of fix-bed reaction, to replenish molybdenum component so that the distribution of the molybdenum component deposited on a catalyst bed will be a desired one. Moreover, there is such a possibility that sublimed molybdenum component is deposited and accumulated in a low-temperature area in the reaction system to cause various troubles, and the replenishment of molybdenum component promotes this tendency.

Thus, in this technical field, there has been a serious demand for developing a molybdenum-containing metallic oxide catalyst from which molybdenum component is not readily lost during reaction and whose excellent activity can be retained for a long period of time without replenishing the molybdenum component, or by replenishing an extremely small amount of the molybdenum component even if the replenishment of the same is needed.

SUMMARY OF THE INVENTION

The present invention has been accomplished in order to overcome the aforementioned shortcomings of the conventional molybdenum-containing metallic oxide catalysts. An object of the present invention is therefore to provide a method for preventing a molybdenum-containing metallic oxide catalyst from losing its molybdenum component while the oxidation (including ammoxidation and oxidative dehydrogenation) of an organic compound is conducted by means of gas phase fluidized-bed reaction at a high temperature, thereby fully retaining the excellent activity of the catalyst.

We found the following in the course of our studies: in the case where the ammoxidation of an olefin is conducted by means of gas phase fluidized-bed reaction using, as a catalyst, a metallic oxide containing molybdenum, bismuth, and one or two elements selected from the group consisting of iron and cerium, if a small amount of tellurium is added to this metallic oxide, the loss of the molybdenum component from the catalyst is considerably prevented during the reaction, and, at the same time, the catalyst life is prolonged. The present invention has been accomplished on the basis of this finding.

The present invention in one aspect thereof is thus a method for retaining the activity of molybdenum-containing oxide catalysts, and in another aspect thereof is a molybdenum-containing oxide catalyst having a molybdenum content of no less than 10% by weight, useful for the oxidation of an organic compound which is conducted by means of gas phase fluidized-bed reaction at a temperature ranging from 300° C. to 500° C., comprising (i) bismuth, (ii) iron and/or cerium, and (iii) tellurium, the atomic ratio of the tellurium to the molybdenum being (0.05–1.5):10.

DETAILED DESCRIPTION OF THE INVENTION

[Catalyst]

In the method of the present invention for retaining the activity of molybdenum-containing oxide catalysts, an important point is to incorporate tellurium into a metallic oxide containing molybdenum, bismuth, and iron and/or cerium. By this, the molybdenum-containing metallic oxide catalyst can be prevented from losing its molybdenum component, and the excellent catalytic activity can thus be retained.

In the case of a catalyst without bismuth, iron or cerium, the catalyst is readily reduced even when tellurium component is added thereto. As a result, metallic tellurium separates out on the surface of the catalyst, or the tellurium component is lost from the catalyst during reaction. The catalysts of this type are thus insufficient in properties as industrial catalysts.

The molybdenum-containing oxide catalysts of the present invention, which have been improved in the retention of catalytic activity, are distinguishable over the previously-mentioned molybdenum-containing oxide catalysts in that their molybdenum contents are 10% by weight or more and that they contain (i) bismuth, (ii) iron and/or cerium, and (iii) tellurium, the atomic ratio of the tellurium to the molybdenum being (0.05–1.5):10.

The molybdenum contents of the catalysts of the present invention are 10% by weight or more, preferably in the range of 10 to 70% by weight.

Tellurium is added to such a molybdenum-containing oxide catalyst so that the atomic ratio of the tellurium to the molybdenum will be (0.05–1.5):10, preferably (0.1–1.0):10.

Examples of preferable catalysts of the present invention include molybdenum-containing metallic oxide compositions represented by the following formula:

wherein

Me represents one or two elements selected from the group consisting of Fe and Ce, Q represents at least one element selected from the group consisting of Be, Mg, Ca, Sr, Ba, Ni and Co, preferably at least one element selected from the group consisting of Mg, Ca, Ba, Ni and Co, R represents at least one element selected from the group consisting of P, B, As, Se, Li, Na, K, Rb, Cs and Tl, preferably at least one element selected from the group consisting of P, B, Li, Na, K, Rb and Cs, X represents at least one element selected from the group consisting of V, W, Y, La, Zr, Hf, Nb, Ta, Zn, Cd, Al, Ga, In, Ge, Sn, Sb and Pb, preferably at least one element selected from the group consisting of V, W, La, Zr, Nb, Ta, Zn, Al, Ga, In, Ge, Sn and Sb, Y represents at least one element selected from the group consisting of Pr, Nd, Sm, Eu, Gd, Th, U, Cr, Mn, Re, Ru, Rh, Pd, Os, Ir, Pt, Cu, Ag and Au, preferably at least one element selected from the group consisting of Pr, Nd, Sm, U, Cr, Mn, Re, Ru, Rh, Pd, Os, Ir, Pt, Cu and Ag, and the indexes a, b, c, d, e, f, g, h and z represent an atomic ratio, and when a=10, b, c, d, e, f, g and h are in the following respective ranges:

0.1≦b≦3, preferably 0.2≦b≦2.5,
0.1≦c≦10, preferably 0.2≦c≦8,
0.05≦d≦1.5, preferably 0.1≦d ≦1.25,
0≦e≦6.75, preferably 0≦e≦6.5,
0≦f≦3, preferably 0≦f≦2, $0 \leq g \leq 8$, preferably $0 \leq g \leq 5$, and
$0 \leq h \leq 0.8$, preferably $0 \leq h \leq 0.7$, and
z indicates the number of oxygen atoms in an oxide formed when the above components are combined.

It has been known that tellurium component is readily reduced and lost more easily than molybdenum component (T. Ohara, M. Hirai, N. Shimizu, Hydrocarbon Processing, November 1972, 85–88). In catalyst systems containing both molybdenum and tellurium, the lowering of catalytic activity caused due to the loss of tellurium has rather been a serious problem.

However, when tellurium was added to a catalyst system containing molybdenum, bismuth, and iron and/cerium, provided that the amount of the tellurium added was small as compared with that of the molybdenum as described above, the loss of the tellurium component itself was prevented, and, at the same time, the loss of the molybdenum component was also prevented. This was a finding unexpected from the conventional knowledge.

The reason for this is not clear, but considered to be as follows: molybdenum contained in molybdenum oxide or in a molybdate is partially replaced with tellurium whose ion radius is almost equal to that of molybdenum to form a solid solution, and the movement of lattice oxygens is thus promoted, whereby the redox stability is increased, and the structural stability is also enhanced.

The formation of a new crystalline phase is not detected when tellurium is added to the catalyst and it is difficult to find a clear change by X-ray powder diffraction method.

In the case where tellurium is added in such an amount that the atomic ratio of the tellurium to the molybdenum will be less than 0.05 to 10, the effect of preventing the loss of molybdenum component is small. On the other hand, when tellurium is added in such an amount that the atomic ratio of the tellurium to the molybdenum will be more than 1.5 to 10, the sintering of the catalyst is promoted. As a result, the reaction rate may be decreased, and the yield of a desired product may be lowered. Further, in the case of ammoxidation reaction, although the effect of preventing the loss of molybdenum component can be confirmed, combustion of ammonia tends to be increased, or the loss of tellurium component tends to be increased.

In the present invention, a specific amount of tellurium component, which has conventionally been considered to be readily reduced and easily lost during reaction, is added to a metallic oxide containing molybdenum, bismuth, and iron and/or cerium. By doing so, the loss of the molybdenum component is remarkably prevented and, at the same time, the loss of the tellurium component is also prevented. The catalyst can thus be drastically prevented from deterioration, and the excellent activity of the catalyst can be retained for a prolonged period of time. In addition, troubles such as the deposition or accumulation of molybdenum component in the reaction system are also decreased. The present invention thus brings about extremely great economical advantages in commercial production.

The catalyst of the present invention shows excellent activity even when it is not supported on a carrier. It is however possible to use the catalyst supported on such a carrier such as silica, alumina, silica-alumina, titania or zirconia, or a mixture thereof. In this case, the amount of the carrier is preferably 10 to 70% by weight of the total weight of the catalyst.

Although the catalyst of the present invention can be used for both fixed-bed reaction and fluidized-bed reaction, it brings about enhanced advantages when used for fluidized-bed reaction. Namely, in fluidized-bed reaction, fluidization of the catalyst of the invention is greatly improved, so that the decrease in performance during the reaction becomes smaller and the operability in pneumatic conveying of particulate catalyst, the flow down of catalyst particles in the dip-leg of a cyclone, and others are also remarkably improved. Further, the deposition or accumulation of molybdenum component in a reactor or heat exchanger, which has often been caused when a molybdenum-containing catalyst is used, is either remarkably lessened or not observed at all according to the present invention. This is also favorable from an industrial point of view.

As fluidized-bed catalysts, particles having a diameter ranging from about 10 to about 500 micrometers are preferably used.

[Application of the catalysts]

It is preferable that the catalyst of the present invention is used for oxidation reaction of an organic compound. The oxidation reaction as used herein means not only simple oxidation but also ammoxidation and oxidative dehydrogenation. Specifically, it is preferable to use the catalyst of the present invention for the production of unsaturated aldehydes, unsaturated nitriles, hydrogen cyanide, aromatic aldehydes, aromatic nitriles, or the like that is conducted by the oxidation, ammoxidation or oxidative dehydrogenation of organic compounds. In general, these reactions are carried out at a temperature ranging from 300° C. to 500° C. In particular, in ammoxidation reactions for producing nitriles, the optimum reaction temperatures are often higher than 400° C., whereby various troubles tend to occur due to the loss of the molybdenum component from the catalyst. Accordingly, it is particularly preferable to use the catalyst of the present invention for the production of nitrites by means of the ammoxidation of olefins, paraffins or alcohols. Preferable reactions for the catalysts of the present invention are, for instance, the ammoxidation of olefins to the corresponding nitrites, specifically the ammoxidation of propylene or isobutene to acrylonitrile or methacrylonitrile, and the ammoxidation of alcohols to the corresponding nitrites, specifically the ammoxidation of methanol to hydrogen cyanide.

[Preparation Methods of the Catalysts]

The catalyst of the present invention can be prepared by any known method. For example, those methods which are described in Japanese Patent Publications No. 8568/1962, No. 49253/1982 (U.S. Pat. No. 3,746,657), No. 12913/1979 and No. 1674/1976 (DE Patent No. 1,542,330), Japanese Patent Laid-Open Publications No. 59046/1990 and No. 214543/1990 (U.S. Pat. No. 5,059,573), and the like can be used.

<Starting Materials of the Catalyst>

Starting materials for each component of the catalyst of the invention can be selected from a great variety of materials such as metal, oxide, hydroxide, chloride and nitrate of each component metal. Further, those compounds which are transformed into oxides when chemically treated or calcined can also be used.

As starting materials for the molybdenum component, there can be used, for example, molybdenum oxide such as molybdenum trioxide, molybdic acid, ammonium paramolybdate, ammonium metamolybdate, and heteropolyacids such as phosphomolybdic acid and silicomolybdic acid and salts thereof.

As starting materials for the bismuth component, there can be used, for example, bismuth salts such as bismuth nitrate and bismuth sulfate, bismuth trioxide, and oxidation products of metallic bismuth with nitric acid.

As starting materials for the iron component, there can be used, for example, iron oxides such as ferrous oxide, ferric oxide and triiron tetroxide, mineral acid salts of iron such as ferrous chloride, ferric chloride, ferric nitrate and iron carbonate, oxidation products of metallic iron with nitric acid, and organic acid salts of iron such as iron oxalate and iron citrate.

As starting materials for the cerium component, there can be used, for example, cerium oxide, cerium hydroxide, cerium sulfate, cerium acetate, cerium nitrate and cerium ammonium nitrate.

As starting material for the tellurium component, there can be used, for example, metallic tellurium, tellurium dioxide, tellurium trioxide, telluric acid and tellurium nitrate.

As starting materials for the cobalt component, there can be used, for example, cobalt oxide, cobalt hydroxide, and oxidation products of metallic cobalt with nitric acid.

As starting materials for the nickel component, there can be used, for example, nickel oxide, nickel hydroxide, nickel nitrate, and oxidation products of metallic nickel with nitric acid.

As starting materials for the vanadium component, there can be used, for example, ammonium metavanadate, vanadyl sulfate, vanadyl oxalate, vanadium pentaoxide and peroxy vanadium compounds.

As starting materials for the tungsten component, there can be used, for example, tungsten trioxide, tungstic acid, tungstates such as ammonium paratungstate and ammonium metatungstate, and heteropolyacids such as phosphotungstic acid and salts thereof.

As starting materials for the other Q, R, X and Y components, oxide, hydroxide, chloride and nitrate of each component can be used.

As starting materials for the carrier, silica sol, silica hydrogel, fumed silica, alumina sol, alumina powder, titania sol, titania powder, and the like can be used.

<Preparation of Catalysts>

A catalyst of the invention can be prepared by mixing the above materials for the catalyst so that the catalyst can have a desired composition, and then drying and calcining the mixture. Regarding the preparation of a fluidized-bed catalyst, it is preferable to spray-dry a slurry prepared by mixing the components of the catalyst to obtain fine spherical particles, and to heat these particles at a temperature ranging from 200 to 800° C., preferably from 400 to 750° C. for 0.5 to 10 hours. The atmosphere in which the calcination is performed is preferably non-reducing, and it may be either an oxidizing atmosphere containing molecular oxygen, or an inert atmosphere of a gas such as nitrogen. It is, however, preferable to perform the calcination in the air for economic reasons. As the calcining apparatus, a tunnel kiln, rotary kiln, fluidized fed celciner or the like can be used.

[Examples]

Embodiments and advantages inherent in the present invention will now be specifically explained by referring to the following examples. However, the present invention is not limited to the examples.

<Test Method of Catalytic Activity>

A fluidized-bed reactor having an inner diameter of 25 mm and a height of 400 mm was filled with a catalyst, and propylene or methanol, ammonia, oxygen and nitrogen were fed to the reactor under the following conditions.

<Test Conditions>

(1) Propylene/ammonia/oxygen/nitrogen (molar ratio) =1/1.2/1.9/7.9; reaction temperature: 420–450° C.; gas linear velocity: 4.5 cm/sec; pressure: 202.6 kPa.

(2) Methanol/ammonia/oxygen/nitrogen (molar ratio) =1/1.0/1.2/4.5; reaction temperature: 420° C.; gas linear velocity: 4.5 cm/sec; pressure: 101.3 kPa.

The conversion of propylene or methanol, and the yield of acrylonitrile or hydrogen cyanide is defined as follows:

Conversion of propylene or methanol (%) ={(number of moles of propylene or methanol consumed by reaction)/(number of moles of propylene or methanol fed)}×100

Yield of acrylonitrile or hydrogen cyanide (%) ={(number of moles of acrylonitrile or hydrogen cyanide produced)/(number of moles of propylene or methanol fed)}×100

<Catalyst 1>

An oxide composition having the empirical formula:

$$Mo_{10}Bi_{0.8}Te_{0.5}Fe_{1.7}Ni_{2.1}Co_{3.75}Mn_{0.8}Cr_{0.4}K_{0.08}O_{42.84}(SiO_2)_{40}$$

was prepared in the following manner. 368.9 g of ammonium molybdate was dissolved in 400 g of pure water by heating, and to this was added 2,511 g of 20% silica sol with stirring. To this solution, a solution of 127.6 g of nickel nitrate, 228 g of cobalt nitrate, 33.4 g of chromium nitrate, 48 g of 50% manganese nitrate and 1.7 g of potassium nitrate in 250 g of pure water was added, and the mixture was stirred. To the mixture, a solution of 81 g of bismuth nitrate, 143.5 g of iron nitrate, 24 g of telluric acid and 30 g of citric acid in 100 g of 10% nitric acid was added with stirring. The pH of the resulting slurry was finally adjusted to 8 by adding 15% aqueous ammonia. This slurry was heated at 100° C. for 1 hour, and then spray-dried by a rotary disc spray dryer whose inlet and outlet temperatures had been adjusted to 320° C. and 160° C., respectively. The particles obtained were heat-treated at 250° C., and then calcined firstly at 400° C. for 2.5 hours and finally 600° C. for 3 hours.

<Catalyst 2>

An oxide composition having the empirical formula:

$$Mo_{10}W_{0.4}Bi_{0.8}Te_{0.25}Fe_{1.6}Ni_{2.0}Co_{3.5}Cr_{0.25}Mn_{0.9}Sm_{0.09}Na_{0.25}K_{0.4}Rb_{0.04}Cs_{0.09}O_{43.5}(SiO_2)_{40}$$

was prepared in the same manner as in the production of Catalyst 1. It is noted that the calcination of the catalyst was performed at 670° C. for 3 hours.

<Catalyst 3>

An oxide composition having the empirical formula:

$$P_{0.25}Mo_{10}Bi_{2.0}Te_{1.0}Fe_{5.5}Ce_{0.5}K_{0.06}O_{44.65}(SiO_2)_{40}$$

was prepared in the same manner as in the production of Catalyst 1. It is noted that the calcination of the catalyst was performed at 690° C. for 3 hours.

<Catalyst 4>
An oxide composition having the empirical formula:

$$P_{0.3}Mo_{10}W_{0.1}Bi_{1.0}Te_{0.25}Fe_{2.0}Mg_{6.0}K_{0.2}O_{42.15}(SiO_2)_{60}$$

was prepared in the same manner as in the production of Catalyst 1. It is noted that the calcination of the catalyst was performed at 600° C. for 3 hours.

<Catalyst 5>
An oxide composition having the empirical formula:

$$P_{0.3}Mo_{10}W_{0.1}Bi_{1.0}Te_{1.5}Fe_{2.0}Mg_{6.0}K_{0.2}O_{44.65}(SiO_2)_{60}$$

was prepared in the same manner as in the production of Catalyst 1. It is noted that the calcination of the catalyst was performed at 600° C. for 3 hours.

<Catalyst 6>
An oxide composition having the empirical formula:

$$Mo_{10}Bi_{0.5}Te_{0.25}Fe_{7.5}O_{42.5}(SiO_2)_{60}$$

was prepared in the following manner.

77 g of 65% nitric acid was mixed with 423 g of pure water. In this mixture, 432.8 g of iron nitrate and 34.6 g of bismuth nitrate were dissolved. To this solution were then added 3,433 g of silica sol and 8.2 g of telluric acid with stirring, and to the resulting mixture was added a solution of 252.2 g of ammonium paramolybdate in 1,000 g of pure water. The mixture was heat-treated at 100° C. for 3 hours. The slurry thus obtained was spray-dried in the same manner as in the production of Catalyst 1, and calcined at 750° C. for 3 hours.

<Catalyst 7>
An oxide composition having the empirical formula:

$$Mo_{10}Bi_{0.8}Fe_{1.7}Ni_{2.1}Co_{3.75}Mn_{0.8}Cr_{0.4}K_{0.08}O_{41.84}(SiO_2)_{40}$$

was prepared in the same manner as in the production of Catalyst 1. It is noted that the calcination of the catalyst was performed at 600° C. for 3 hours.

<Catalyst 8>
An oxide composition having the empirical formula:

$$Mo_{10}W_{0.4}Bi_{0.8}Fe_{1.6}Ni_{2.0}Co_{3.5}Cr_{0.25}Mn_{0.9}Sm_{0.09}Na_{0.25}K_{0.4}Rb_{0.04}$$

$$Cs_{0.09}O_{43.0}(SiO_2)_{40}$$

was prepared in the same manner as in the production of Catalyst 1. It is noted that the calcination of the catalyst was performed at 670° C. for 3 hours.

<Catalyst 9>
An oxide composition having the empirical formula:

$$P_{0.25}Mo_{10}Bi_{2.0}Fe_{5.5}Ce_{0.5}K_{0.06}O_{44.15}(SiO_2)_{60}$$

was prepared in the same manner as in the production of Catalyst 1. It is noted that the calcination of the catalyst was performed at 690° C. for 3 hours.

<Catalyst 10>
An oxide composition having the empirical formula:

$$P_{0.3}Mo_{10}W_{0.1}Bi_{1.0}Te_{0.01}Fe_{2.0}Mg_{6.0}K_{0.2}O_{41.67}(SiO_2)_{60}$$

was prepared in the same manner as in the production of Catalyst 1. It is noted that the calcination of the catalyst was performed at 600° C. for 3 hours.

<Catalyst 11>
An oxide composition having the empirical formula:

$$P_{0.3}Mo_{10}W_{0.1}Bi_{1.0}Te_{2.0}Fe_{2.0}Mg_{6.0}K_{0.2}O_{45.65}(SiO_2)_{60}$$

was prepared in the same manner as in the production of Catalyst 1. It is noted that the calcination of the catalyst was performed at 600° C. for 3 hours.

<Catalyst 12>
An oxide composition having the empirical formula:

$$Mo_{10}Bi_{0.5}Fe_{7.5}O_{42.0}(SiO_{280})$$

was prepared in the same manner as in the production of Catalyst 6. It is noted that the calcination of the catalyst was performed at 750° C. for 3 hours.

EXAMPLES 1 TO 5 & COMPARATIVE EXAMPLES 1 TO 5

With the above-described Catalysts 1 to 5 (Examples 1 to 5) and Catalysts 7 to 11 (Comparative Examples 1 to 5), the ammoxidation of propylene was conducted under the previously-mentioned test conditions. The results are in Table 1.

TABLE 1

| Test Example | Catalyst | Contact time (sec) | After 50-hour reaction | | After 500-hour reaction | |
|---|---|---|---|---|---|---|
| | | | Conversion of PP (%) | Yield of AN (%) | Conversion of PP (%) | Yield of AN (%) |
| Example | Catalyst | | | | | |
| 1 | 1 | 4.50 | 96.0 | 76.7 | 93.5 | 75.2 |
| 2 | 2 | 4.25 | 96.2 | 79.2 | 94.3 | 77.6 |
| 3 | 3 | 4.75 | 95.5 | 75.9 | 94.9 | 75.3 |
| 4 | 4 | 2.75 | 96.2 | 78.8 | 95.3 | 77.9 |
| 5 | 5 | 3.00 | 96.0 | 78.5 | 95.8 | 78.2 |
| Comparative Example | Catalyst | | | | | |
| 1 | 7 | 4.50 | 96.2 | 77.0 | 92.5 | 74.1 |

TABLE 1-continued

| Test Example | Catalyst | Contact time (sec) | After 50-hour reaction | | After 500-hour reaction | |
|---|---|---|---|---|---|---|
| | | | Conversion of PP (%) | Yield of AN (%) | Conversion of PP (%) | Yield of AN (%) |
| 2 | 8 | 4.25 | 96.5 | 79.0 | 93.2 | 76.2 |
| 3 | 9 | 4.75 | 95.9 | 76.3 | 93.5 | 74.0 |
| 4 | 10 | 2.75 | 96.3 | 78.5 | 94.1 | 76.3 |
| 5 | 11 | 3.00 | 95.8 | 78.0 | 95.5 | 77.7 |

Note)
"PP" is an abbreviation of propylene.
"AN" is an abbreviation of acrylonitrile.

EXAMPLE 6 & COMPARATIVE EXAMPLE 6

With the above-described Catalyst 6 (Example 6) or Catalyst 12 (Comparative Example 6), the ammoxidation of methanol was conducted under the previously-mentioned test conditions. The results are shown in Table 2.

TABLE 2

| Test Example | Catalyst | Contact time (sec) | After 50-hour reaction | | After 500-hour reaction | |
|---|---|---|---|---|---|---|
| | | | Conversion (of ME (%) | Yield of HCN (%) | Conversion of ME (%) | Yield of HCN (%) |
| Example | Catalyst | | | | | |
| 6 | 6 | 0.3 | 98.4 | 88.5 | 98.5 | 88.3 |
| Comparative Example | Catalyst | | | | | |
| 6 | 12 | 0.3 | 98.8 | 89.1 | 97.8 | 87.1 |

Note) "ME" is an abbreviation of methanol.

[Discussion]

The activity of the catalysts of the present invention is highly stable for a long period when used in oxidation reaction such as the ammoxidation reaction of propylene and that of methanol as compared with the activity of the catalysts used in Comparative Examples 1, 2, 3 and 6, containing no tellurium. Further, after the reactions were carried out with the catalysts of the present invention, it was confirmed that almost no molybdenum component was deposited on the upper part of the reactor. Furthermore, the catalysts of the invention, drawn out from the reactor after the reactions were excellent in fluidity, and the results of the analysis of the composition of these catalysts showed almost no change in both molybdenum and tellurium content.

On the contrary, after the reaction carried out in Comparative Example 1, 2, 3 or 6, with a catalyst containing no tellurium component, or in Comparative Example 4 with a catalyst containing only a small amount of tellurium component, it was found that white molybdenum oxide was deposited on the upper part of the reactor. The molybdenum oxide was collected and weighed. As a result, the weight was 0.12 g in the case of Comparative Example 1, and 0.1 g in the case of Comparative Example 4. Further, the catalysts used in Comparative Examples 1, 2, 3 and 6, drawn out from the reactor after the reactions were found to have considerably lowered fluidity. Furthermore, after the reaction carried out in Comparative Example 5 with a catalyst having a high tellurium content, Catalyst 11, the deposition of metallic tellurium was found at the upper part of the reactor.

What is claimed is:

1. A method for ammoxidation of propylene, which comprises subjecting propylene, ammonia and oxygen to gas phase fluidized-bed reaction at a temperature ranging from 300 to 500° C. in the presence of a molybdenum-containing oxide catalyst having a molybdenum content of no less than 10% by weight, further comprising:
   (i) bismuth,
   (ii) iron and/or cerium, and
   (iii) tellurium, the atomic ratio of the tellurium to the molybdenum being (0.05–1.5):10.

2. The method according to claim 1, wherein the catalyst has a composition represented by the following formula:

$$Mo_a Bi_b Me_c Te_d Q_e R_f X_g Y_h O_z$$

wherein
Me represents one or two elements selected from the group consisting of Fe and Ce;
Q represents at least one element selected from the group consisting of Be, Mg, Ca, Sr, Ba, Ni and Co;
R represents at least one element selected from the group consisting of P, B, As, Se, Li, Na, K, Rb, Cs and Tl;
X represents at least one element selected from the group consisting of V, W, Y, La, Zr, Hf, Nb, Ta, Zn, Cd, Al, Ga, In, Ge, Sn, Sb and Pb;
Y represents at least one element selected from the group consisting of Pr, Nd, Sm, Eu, Gd, Th, U, Cr, Mn, Re, Ru, Rh, Pd, Os, Ir, Pt, Cu, Ag and Au; and
the indexes a, b, c, d, e, f, g, h and z represent an atomic ratio where a, b, c, d, e, f, g and h are in the following respective ranges:
a=10, $0.1 \leq b \leq 3$, $0.1 \leq c \leq 10$, $0.05 \leq d \leq 1.5$, $0 \leq e \leq 6.75$, $0.08 \leq f \leq 0.78$, $0 \leq g \leq 8$, and $0 \leq h \leq 0.8$, and z indicates the number of oxygen atoms in an oxide formed when the above components are combined.

3. The method according to claim 2, wherein the indexes a to h are in the following respective ranges:

a: 10;
b: 0.2 to 2.5;
c: 0.2 to 8;
d: 0.1 to 1.25;
e: 0 to 6.5;
f: 0.08 to 0.78;
g: 0 to 5; and
h: 0 to 0.7.

* * * * *